United States Patent
Janunts et al.

(10) Patent No.: US 10,694,938 B2
(45) Date of Patent: Jun. 30, 2020

(54) PURKINJE METER AND METHOD FOR AUTOMATIC EVALUATION

(71) Applicant: JANUNTS HOLDING UG (haftungsbeschränkt), Saarbrücken (DE)

(72) Inventors: Edgar Janunts, Saarbrücken (DE); Dominic Putzu, Wadgassen (DE); Janine Van Bellen, Trier (DE); Michael Möller, Saarbrücken (DE); Achim Langenbucher, Kirrberg (DE)

(73) Assignee: JANUNTS HOLDING UG (HAFTUNGSBESCHRANKT), Saarbrucken (DE)

(*) Notice: Subject to any disclaimer, the term of this patent is extended or adjusted under 35 U.S.C. 154(b) by 116 days.

(21) Appl. No.: 15/740,935

(22) PCT Filed: Jun. 28, 2016

(86) PCT No.: PCT/EP2016/065054
§ 371 (c)(1),
(2) Date: Dec. 29, 2017

(87) PCT Pub. No.: WO2017/001426
PCT Pub. Date: Jan. 5, 2017

(65) Prior Publication Data
US 2018/0338678 A1    Nov. 29, 2018

(30) Foreign Application Priority Data
Jun. 29, 2015 (DE) .................. 10 2015 110 456

(51) Int. Cl.
*A61B 3/14* (2006.01)
*A61B 3/10* (2006.01)
(Continued)

(52) U.S. Cl.
CPC .......... *A61B 3/1005* (2013.01); *A61B 3/0008* (2013.01); *G06T 7/70* (2017.01); *A61B 3/113* (2013.01)

(58) Field of Classification Search
CPC ... A61B 3/0008; A61B 3/0025; A61B 3/0091; A61B 3/024; A61B 3/1005;
(Continued)

(56) References Cited

U.S. PATENT DOCUMENTS

2008/0204657 A1* 8/2008 Neuhann ............... A61B 3/113
351/210
2014/0268042 A1* 9/2014 Bor ........................ A61B 3/14
351/206

FOREIGN PATENT DOCUMENTS

| EP | 2604180 A1 | 6/2013 |
| JP | 2014052813 A | 3/2014 |
| WO | 2014073645 A1 | 5/2014 |

OTHER PUBLICATIONS

Tabernero, J., et al., "Instrument for Measuring the Misalignments of Ocular Surfaces," Optics Express, vol. 14, No. 22, p. 10945, Oct. 30, 2006.
(Continued)

*Primary Examiner* — Mustak Choudhury
(74) *Attorney, Agent, or Firm* — James E. Walton

(57) ABSTRACT

The invention relates to a new type of measurement method for automatically recording and evaluating the Purkinje reflections of an eye in order to determine the malposition (decentration and tilt) of intraocular or natural lenses and to a device for applying said method. According to the invention, the eye is systematically illuminated from different directions and, by means of linear regression, the relative lens orientation is extracted from the position of the Pukinje reflections thus produced.

12 Claims, 2 Drawing Sheets

(51) Int. Cl.
*A61B 3/00* (2006.01)
*G06T 7/70* (2017.01)
*A61B 3/113* (2006.01)

(58) Field of Classification Search
CPC .......... A61B 3/1015; A61B 3/12; A61B 3/14;
A61B 3/103; A61B 3/107; A61B 3/113;
A61B 3/158; A61B 3/165; A61B 3/10;
A61F 9/007; A61F 9/00804; A61F
9/00806; A61F 2/14; A61F 2/16; A61F
2/142; A61F 2/4851; G06T 7/70
USPC ........................................................ 351/206
See application file for complete search history.

(56) References Cited

OTHER PUBLICATIONS

Schaeffel, F., "Binocular Lens Tilt and Decentration Measurements in Healthy Subjects with Phakic Eyes," Investigative Ophthalmology & Visual Science, vol. 49, No. 5, p. 2216, May 2008.
International Search Report dated May 10, 2016 from parent Int'l Appl. No. PCT/EP2016/065054.

* cited by examiner

PURKINJE METER AND METHOD FOR AUTOMATIC EVALUATION

FIELD OF THE INVENTION

The invention relates to the field of image acquisition and image recognition in the field of opthalmological diagnostics.

STATE OF THE ART

A cataract is a clouding of the eye lens. A natural cloudy eye lens can be surgically removed and replaced with a lens implant, also known as an intraocular lens, IOL. The vision of the treated eye depends on the quality and geometry of the implanted lens, but also on its position or position in the eye.

Decentering or tilting the lens can result in significant vision impairment after surgery. This is even more relevant if the implanted lens has a geometry specifically adapted to the eye. For aspherical lens implants, for example, critical tilt values of +/−7° and decentration values of +/−0.4 mm are known.

Therefore, it is important to be able to detect the position of an intraocular lens as simply and accurately as possible in order to be able to correctly deduce the cause of such an impairment. Known methods for determining the position in an eye include optical coherence tomography (OCT), Scheimpflug methods, ultrasound biomicroscopy, and Purkinjemetry.

Purkinjemetry is based on the recognition that light rays that enter the eye are reflected at different interfaces at different angles. This makes the Purkinje pictures visible. These are the images produced by reflecting the light rays on the various refractive surfaces of the cornea and the crystalline body or lens. With reference to FIG. 1, the Purkinje reflexes are explained in more detail. The first image, P1, is the reflection that develops on the anterior corneal surface of the cornea 1. P2 is created on the posterior surface of the cornea and usually overlaps with P1, so that P2 is usually irrelevant for further calculations. The third image, P3, is formed on the front lens surface of the lens 2, and P4 is finally formed on the rear lens surface.

It is known that due to the relative position of the Purkinje images, magnitudes such as e.g. the distance between the lens and the iris or the curvature of the lens can be calculated.

To the best of Applicants' knowledge, two Purkinje meters, that is, devices for detecting and evaluating Purkinje reflections, are currently known. A first Purkinje meter was disclosed by Tabarnero and Artal (Tabarnero et al., Instrument for measuring the misalignment of ocular surfaces, Opt Express, 2006; 14: 10945-10956). Here, it is known that a plurality of semicircular light sources are provided for illuminating the eye used in different positions. The corresponding Purkinje reflexes P1, P3, and P4 generally do not conform to the shape of the projected semicircular patterns because they are deformed by individual corneal and lens geometries. A pattern recognition by assuming a predefined form is therefore subject to a systematic error.

A second Purkinje meter was developed by F. Schaeffel (Schaeffel, Binocular lens tilt and decentration measurements in healthy subjects with phakic eyes, Invest Ophtalmol Vis Sci 2008, 49: 2216-2222). The procedure for detecting Purkinje reflexes usually takes about 10 minutes. It uses a single light source to illuminate the eye. The examined person is asked to stare at various predetermined reference points to detect the corresponding different positions of the reflections P1, P3, P4 by manually triggering a camera. The detected reflexes are then manually assigned to the Purkinje reflexes P1, P3 and P4 to the knowledge of the examiner. Any mistake made by the subject or investigator during the procedure will result in the procedure having to be restarted. Thus, this Purkinje meter is difficult to use, at least in non-cooperative patients.

Both of the known devices and the underlying methods are based on the fact that the patient to be examined for each individual measurement (an investigation consists of a series of manual individual measurements) must focus different points in different directions. Thus, the quality of the measurement depends crucially on the willingness of the patient to cooperate and the accuracy/stability of his or her focus. The susceptibility to error increases with the duration of the examination, which can be several minutes. In addition, the image analysis is performed manually, and the mapping of reflected reflections to the Purkinje reflections depends on the experience of the image analyst.

The object of the invention is therefore to provide a Purkinje meter and a corresponding method which overcomes at least one of the disadvantages mentioned in this application.

DISCLOSURE OF THE INVENTION

The formulated technical problem is solved by the features of the device according to the invention and of the method according to the invention. The invention relates to a device for imaging an eye in an image sequence. The device comprises:

- a camera, which comprises imaging means and a camera lens, and defines a camera axis;
- positioning means which are adapted to bring the camera relative to the eye to be imaged in a fixed, predetermined position;
- a plurality of individual light sources, which are arranged so that each of the light sources can emit light beams at a respectively predetermined angle with respect to the camera axis and in the direction of the eye to be imaged;
- control means which are configured, by means of the camera with constant position of the camera and the light sources, to capture an image sequence of the eye to be imaged and to secure it on a storage medium.

The control means are adapted to switch on and off the light sources so that, during the capture of the images, the light sources are turned on in a predetermined order and that only one predetermined light source is turned on during the detection of each of the images.

Preferably, the light sources can be arranged around the camera lens along at least one arc of a circle. Advantageously, the light sources can be arranged in two arcs concentric, symmetrical with respect to an axis extending centrally through the camera lens and perpendicular to the camera axis.

The light sources can preferably be arranged on an annular surface, or a partially annular surface, that is oriented obliquely to the camera axis.

The light sources may preferably be arranged so that emitted light beams can impinge at right angles and with high probability the cornea of the eye to be imaged.

The plurality of light sources may include, for example, fifteen light sources.

Preferably, the light sources may be infrared light emitting diodes. The imaging means may preferably be infrared-sensitive imaging means.

The light sources can preferably be arranged on a carrier plate.

The carrier plate may further comprise a single visually recognizable reference point.

Preferably, the carrier plate may comprise an additional light source capable of emitting visible light and which is adapted to be turned on during the detection of each of the images.

Alternatively, the device may comprise a single visually detectable reference point outside the carrier plate at a predetermined position. The reference point may be an additional light source which can emit visible light and which is arranged to be turned on during the detection of each of the images. The visible light which is emitted by this reference light source can preferably be introduced via optical means into the field of view of the eye to be imaged. The optical means comprise for example at least one mirror.

The device may additionally comprise processing means which are adapted to recognize individual imaged light reflexes on the images of the image sequence and their displacement along the image sequence.

The processing means may preferably be set up to associate, on the basis of the recognized shape and displacement of the corresponding light reflexes, these with at least one specific Purkinje reflex.

Further, the processing means may be adapted to conclude a position of an intraocular or a natural lens in the imaged eye due to the associated Purkinje reflexes.

The invention also relates to a method for automatically detecting the position of an intraocular lens or a natural lens in an eye on the basis of an image sequence acquired by means of the device according to the invention, which images the eye.

The method comprises the following steps:
recognition of individual imaged light reflexes and their displacement along the image sequence;
assigning at least one of the light reflexes to a Purkinje reflex, by means of the recognized shape and the displacement of the respective light reflexes, as well as the predetermined angle of the respectively corresponding light source, which was switched on during the capture of a respective image;
calculating the decentration and/or tilt of the lens based on the assigned Purkinje reflexes.

Furthermore, an outline of the pupil and/or the iris of the imaged eye is preferably automatically recognized in the image sequence.

Preferably, the subject imaged in the image sequence during image acquisition stares at a single reference point, which is preferably part of the device.

All features of the embodiments described above can be combined with each other or replaced.

BRIEF DESCRIPTION OF THE FIGURES

The figures of the exemplary embodiments will be briefly described below. Further details can be found in the detailed description of the embodiments.

DETAILED DESCRIPTION OF THE EMBODIMENTS

Figure 1:
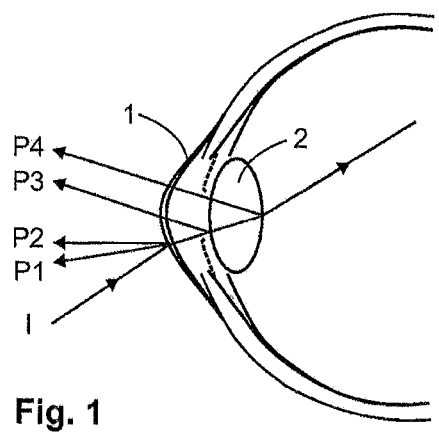
FIG. 1 shows a schematic illustration of an eye and illustrates the known development of the Purkinje reflexes P1, P2, P3 and P4.

FIG. 1 has already been described in the prior art.

Various features are disclosed for clarity in isolation or in combination with other features within a specific embodiment. However, the isolated features of a combination, as well as the combinations of features presented as isolated, are also to be considered disclosed unless it is clearly stated that this is not the case.

The description is not to be construed as limiting the invention and is limited to features that contribute to the understanding of the invention. Known measures, such as the power supply of light sources, or the data connections between various electronic components of the device will not be further described.

Figure 2:
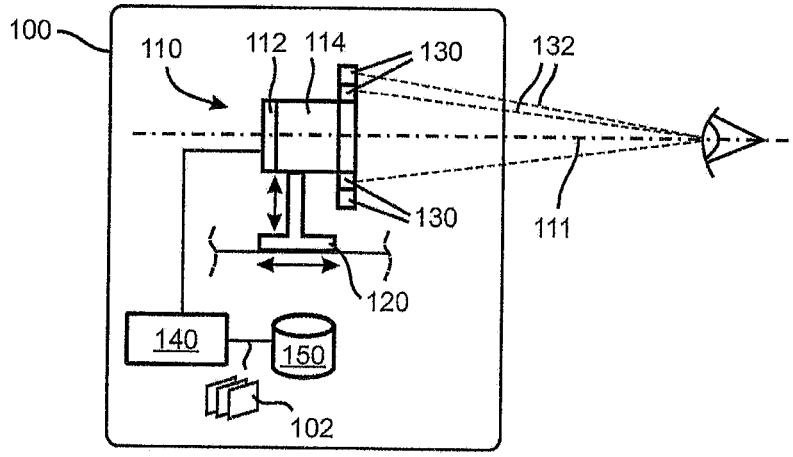
FIG. 2 shows a schematic side view of a device according to the invention in a preferred embodiment.

FIG. 2 shows a preferred embodiment of a device 100 according to the invention. The device is used to image an eye in an image sequence. For this purpose, a camera 110 is used which comprises imaging means 112 and a camera lens 114. The camera lens defines the field of view, which can be imaged using the imaging means 112. The imaging means preferably comprise a matrix of CMOS sensors which can convert incident light into digital signals.

The device comprises positioning means 120, which are designed to bring the camera 110 relative to the eye to be imaged in a fixed, predetermined position. In FIG. 2, the positioning means 120 are represented by a stand which allows to change the height of the camera relative to a horizontal plane, e.g. a table, and/or to change the distance from the eye to be imaged to bring it into the focal plane of the camera.

The device may preferably have means, not shown, for determining the position of the person to be examined, e.g. in the form of a chin and/or forehead support. As an alternative to the illustrated means 120, the person to be examined can likewise be movable relative to the camera.

In order to make the method meaningful, it is preferred that the pupil axis or the line of sight of the eye substantially coincide with the camera axis 111.

A plurality of individual light sources 130 are arranged so that each of the light sources can emit light beams at a respectively predetermined angle with respect to the camera axis 111, the pupil axis or the line of sight, and in the direction of the eye to be imaged. The device preferably comprises an unillustrated storage element which associates a unique identification number of each of the light sources with their predetermined angle with respect to the camera axis 111, the pupil axis or the line of sight. This data can be stored, for example, in a table or a database. The light sources are preferably light emitting diodes, LED, and preferably emit light rays in the infrared range, i.e. in the non-visible part of the light spectrum. This has the advantage that a light beam striking the pupil does not cause it to constrict. Of course, the imaging means 112 are adapted in their photosensitivity to the spectrum of the light sources.

Preferably, individual LEDs with a small emission angle are used. As a result, the positions of the Purkinje reflexes are clearly defined, so that the focal points of the light reflections are better to recognize and the likelihood of overlapping of different reflections is reduced. This simplifies the automatic position detection of the Purkinje reflexes. In addition, by using individual LEDs with a low beam angle, the intensity of the LED can be kept small, and thus the energy input into the eye can be reduced.

The light sources may be fixed in any predetermined manner opposite the camera axis, e.g. along a line which lies within a plane oriented normal to the camera axis and which preferably runs concentrically around the camera lens in a circular manner. The corresponding sector in the case is preferably limited such that the Purkinje reflexes arising from the light rays incident on the eye appear with a high probability within the pupil surface. In the case of incidence of light at larger angles, there is a risk that not all three Purkinje reflexes fall into the field of vision of the iris, which makes positioning or evaluation more difficult.

The device 100 comprises control means 140, e.g. a programmed computer processor, which are designed by means of the camera 110, while maintaining the position of the camera 110 and the light sources 130, to capture an image sequence 102 of the eye to be imaged and to secure it on a storage medium 150. Such means are known per se and a corresponding computer program can be written without inventive step on the basis of this description by a person skilled in the art. The control means 140 are programmed to turn on and off the light sources 130 so that, during the capture of the images, the light sources are turned on in a predetermined order, and that only one predetermined light source 130 is turned on during the detection of each of the images. Preferably, the eye on each captured image is selectively illuminated by a single and different light source. The imaged eye, and the reflections visible therein, can thus be unambiguously assigned to a light entry angle. For each of the stored images, it is preferable to additionally store associated information about the light source switched on during the imaging.

Preferably, the light sources are arranged around the camera lens along at least one arc of circle. For example, the light sources may be arranged on an annular surface or partial annular surface of a carrier plate oriented at an angle to the camera axis. The arrangement is to be chosen so that a constant brightness of the resulting Purkinje reflexes is ensured. It should be noted that the light from the respective direction perpendicular to the corneal surface is incident into the eye. For this purpose, the support plate preferably has a corresponding convex curvature. Constant brightness of different images in the image sequence facilitates automatic recognition of the Purkinje reflexes and makes post-processing of the images at best superfluous.

The carrier plate, on which the infrared LEDs are arranged, additionally comprises a single visually recognizable reference point in a preferred embodiment. This reference point is continuously focused during image acquisition by the eye to be imaged, while in a predetermined order light of the infrared LEDs from different angles is incident into the eye. The reference point may preferably be an additional light source which can emit visible light and which is arranged to be on during the detection of each of the images.

Alternatively, a device according to the invention outside the carrier plate at a predetermined position may comprise this single visually recognizable reference point. The reference point may be an additional light source which can emit visible light and which is arranged to be turned on during the detection of each of the images. The visible light which is emitted by this reference light source can preferably be introduced via optical means into the field of view of the eye to be imaged. The optical means comprise for example at least one mirror. The provision of a reference point is independent of other features according to the invention and can be provided in all embodiments according to the invention.

Figure 3:
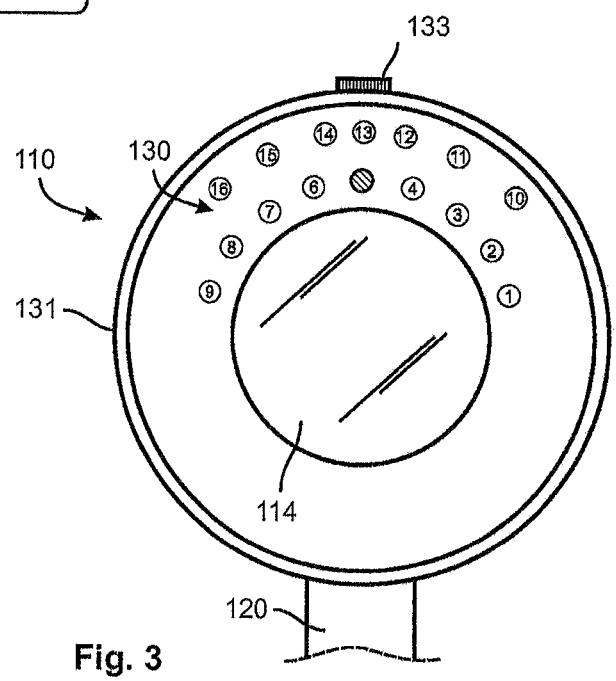
FIG. 3 shows a detail of a preferred embodiment of the device according to the invention.

FIG. 3 shows an example of an annular support plate 131 which can be mounted around a camera lens 114 by means of a set screw 133. The plate comprises the light sources 130 and in particular fifteen infrared LEDs (1-4 and 6-16) and a green LED which is hatched and serves as a reference point.

In order for the pupil recognition (center of the pupil to be the reference for all parameters) to take place automatically, a sufficient SNR ("signal-to-noise ratio") must be ensured. For this purpose, a sufficiently homogeneous illumination of the eye is necessary. This is decoupled from the infrared LEDs 130 and is preferably carried out by an indirect illumination of the eye by means of additional infrared LEDs.

In a preferred embodiment, the device according to the invention additionally comprises image processing means which are adapted to recognize individual imaged light reflections and their displacement along the image sequence on the images of the image sequence. The image processing means are preferably implemented together with the control means 140 by a suitably programmed computer processor.

The automatic recognition method according to the invention for the position of an intraocular or a natural lens is based on the following findings in comparison with the prior art. Single images are not sufficient to assign the different reflexes to the Purkinje reflexes. Only a comparison of different images of a sequence of images, which shows reflections from different predefined lighting directions, allows a reliable assignment. In addition, "false" reflections (scattered light) of Purkinje reflexes can only be reliably distinguished when the latter shift by varying the illumination direction, while reflections of a nonspecific scattered light remain stationary.

The method according to the invention is based on an image sequence acquired by means of the device according to the invention, which images the eye focusing a fixed reference point.

In a first step, individual imaged light reflections and their displacement along the image sequence are detected or identified.

By means of the recognized form and the shift of the corresponding light reflections, and by knowing from which angle the eye was illuminated in each image of the image sequence, different light reflections are assigned to the Purkinje reflexes.

Using the known calculation methods, the decentration and/or tilting of the natural or intraocular lens is then calculated on the basis of the associated Purkinje reflexes.

An automatic recognition of the imaged pupil surface, which may for example be partially covered by an eyelid, can be used to adapt the selection of the light sources 130 used to illuminate the eye, so that the imaged reflections remain with high probability to be evaluated.

On the basis of the measures according to the invention, a measurement can be completed within a few seconds, within which the patient only has to focus a single point for a fraction of a second. The error rate of the method is thus minimal.

In the following, a preferred embodiment of the Purkinje reflex detection method according to the present invention will be explained.

Image Capture

On the basis of a preferred embodiment of the device according to the invention, the eye is illuminated during the acquisition of the image sequence by means of the LED ring 131 shown in FIG. The distance between the camera lens and the eye to be detected is approximately 35 cm. The entire capture procedure produces sixteen grayscale 8-bit images with a 640×480 pixel image, corresponding to 15 infrared LEDs, in which each image has only one infrared LED turned on, and an additional dark image with all infrared LEDs turned off are.

Image Analysis

The algorithm for the automatic detection of Purkinje reflexes consists of three consecutive steps: pupil detection, particle detection (reflex detection) and particle analysis (reflex analysis). First, the pupil must be recognized and extracted along with its center coordinates in each image. This information can be used to reduce the images to the pupil area. In the next step, only the pupil area is considered for searching the Purkinje reflexes. In addition to the Purkinje reflexes, the image may contain artifacts in the form of bright spots. All illuminated dots are treated like a cloud of particles. After detection of the particles their coordinates are analyzed. The Purkinje reflexes P1, P3 and P4 are then recognized. The next step involves the calculation process, which uses the coordinates of the Purkinje reflexes to calculate the position and orientation of the natural or intraocular lens.

Pupil Detection

The pupil detection algorithm uses a simple thresholding technique based on image histograms, which indicate the number of pixels for each gray level. Although they vary in proportion and size, some image features can be found in all images of the captured image sequence that depict the properly-lit eye. The portion of the grayscale pixels that includes the iris and the eyelids is typically in the range of up to 100. These pixels are extracted from the image and the edge of the pupil is detected using a Canny filter. The actual values of course depend on the brightness of the images obtained.

Based on this information, the pupil can best be described using a rotated ellipse. Parameters of the ellipse such as its center and edge can be expressed mathematically in a known manner.

Reflex Recognition

The second stage of image processing involves the detection of the Purkinje reflexes in each of the images captured by the inventive device. The Purkinje reflexes P1, P3, and P4 typically have characteristics that are helpful in detecting them. P1 can often be easily recognized by its star-shaped appearance, often P3 appears larger than P1 and more diffuse. P4 in most cases is approximately circular and considerably smaller than the other two reflexes. In images of pseudophakic eyes, that is, eyes implanted with intraocular lenses, often the three reflexes are observed with similar brightness.

Frequently, additional particles or reflections in the image sequence are detected, so that first all particles within the pupil area must be detected. The main reasons for this are reflections, which are caused by non-ideal light conditions in the examination room as well as bright areas of the iris and other areas of the eye at the edge of the ellipse.

It is assumed that the Purkinje reflections comprise the brightest pixels in the pupil area. The removal of isolated bright pixels may optionally be required in a subsequent step. The last part of this step requires the application of a per se known method for determining the coordinates of each reflex through all the images.

Assigning Reflections to Corresponding Purkinje Reflexes

As already described, the position of the Purkinje reflexes shifts with each individual infrared LED illumination. The movement of the Purkinje reflexes through the images corresponds to the two semi-circles LED on the LED ring.

Figures 4A, 4B:
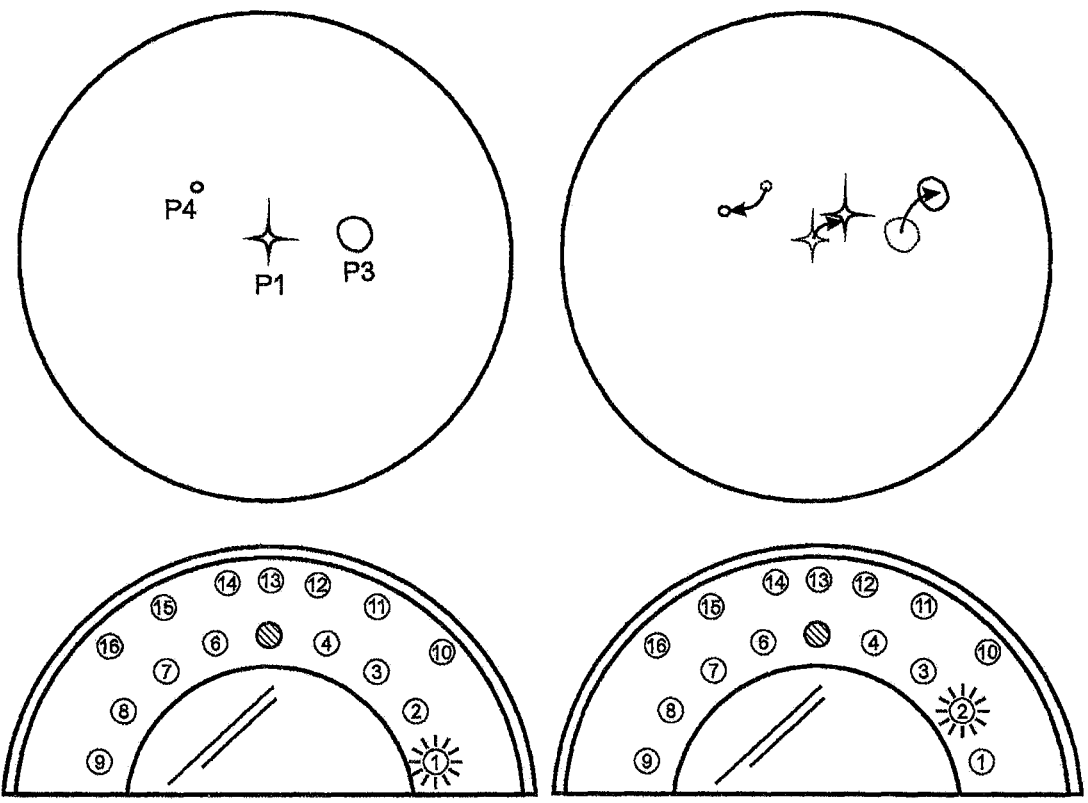
FIG. 4A is a schematic representation of an image (above) depicting an eye detected by the apparatus of the invention in a preferred embodiment; below, the corresponding illumination is shown.
FIG. 4B is a schematic representation of an image (above) depicting an eye detected by the apparatus of the invention in a preferred embodiment; below is the corresponding lighting shown.

In the schematic representation of the pupil area in FIGS. 4A and 4B, it is shown that P4 moves in the direction of the left pupil edge when the LEDs 1 and 2 are switched on successively as shown. P4 reflexes produced by illumination from the bottom semicircle of the LED ring appear below the locations of the reflections resulting from the top semi-circle.

Regarding the position of P1 and P3, the opposite can be observed. They move in the direction of the right pupil margin. Reflexes resulting from the illumination of a light source of the lower row of LEDs appear above the corresponding reflexes, which result from illumination from the upper row. It is important to note that the exact locations and order of the reflexes seen in this schematic depiction are highly dependent on the characteristics of the eye being measured.

Tracking the reflexes begins in the first image. For each of the subsequent images, reference is made to the respective positions of P1, P3 and P4 in the previous image. In particular, the immediate proximity of the position of the three points in the previous image is analyzed.

First, the first detected reflex of the image associated with the LED 1 is considered as an original particle. In the next image, a similar size around the position of the original particle is searched for similarly large particles. If one or more such particles are found within the search scope, they will be used as original particles in the following iteration. If no particles are found, the particles of the entire next image whose size is close to the size of the original particle are selected as the next original particles. This process is repeated until the image of LED #16 is reached. After this cycle is completed for the first particles in the first image, the entire process is repeated for all the remaining particles in the image associated with the LED 1. Finally, for each particle in the image associated with the LED, a set or group of corresponding particles have been identified in the following images.

As shown in FIG. 3, a gap between LED #4 and LED #6 can be observed in the arrangement of the LEDs on the LED ring. In such a case, the search amount for the particles of the respective images can be increased accordingly.

In a following step, it is decided which particles correspond to a Purkinje reflection. The method differentiates between P1, P3 and P4 considering their particular properties, such as size, direction and the distances they travel from one image to the next.

For example, P4 moves counterclockwise and typically has a similar size along the image sequence. Therefore, to recognize the P4 reflex from one image to another, those particles whose size changes least are used. This procedure is repeated for each of the previously identified groups of particles to identify P4 with high probability.

Similar to the previous step for identifying the P4 reflex, characteristic features of the Purkinje reflections P1 and P3 are used to detect them. As both reflections move in the direction of the right pupil edge, the shift distances vary from one image to the next. Normally, P3 reflexes cover larger distances compared to P1. Calculating the appropriate distances for each image then provides a robust method for determining the reflexes in a final step.

LIST OF REFERENCE NUMBERS 1 cornea
2 lens
100 device
102 image sequence
110 camera
111 camera axis
112 imaging agents
114 camera lens
120 positioning means
130 light sources
131 support plate
140 control means
150 storage medium

The invention claimed is:

1. A device for automatically detecting the position of an intraocular lens or a natural lens in an eye, comprising:
   a camera comprising a camera lens and a camera axis;
   a positioning unit adapted to bring the camera relative to the eye to be imaged in a fixed, predetermined position;
   a plurality of individual light sources, which are arranged so that each of the light sources can emit light beams at a respective predetermined angle with respect to the camera axis and in the direction of the eye to be imaged; and
   a control unit which is configured with a constant position of the camera and the light sources, to capture an image sequence of the eye to be imaged and to secure said sequence on a non-transitory storage medium;
   wherein the control unit is configured to switch the light sources on and off so that during capture of the images, the light sources are turned on in a predetermined order and that during the capture of each of the images only one predetermined light source is turned on;
   wherein the control unit is further configured to recognize individual imaged light reflections and their displacement along the image sequence; assign at least one of the light reflections to a Purkinje-reflex by a recognized shape and the displacement of the corresponding light reflections and the predetermined angle of the respectively corresponding light source, which was switched on during the capture of a respective image; and calculate the decentration and/or tilt of the lens based on the assigned Purkinje reflexes; and
   wherein the light sources are arranged around the camera lens along at least one arc of circle.

2. The device according to claim 1, wherein the light sources are arranged on an annular surface, or partial annular surface, obliquely oriented to the camera axis.

3. The device according to claim 1, wherein the light sources are infrared light emitting diodes and wherein the camera comprises an infrared sensitive imaging sensor.

4. The device according to claim 1, wherein the light sources are arranged on a support plate.

5. The device according to claim 4, wherein the device comprises:
   a single visually recognizable reference point.

6. The device according to claim 5, wherein the single visually recognizable reference point is on the support plate.

7. The device according to claim 5, wherein the support plate comprises:
   an additional light source capable of emitting visible light.

8. The device according to claim 7, wherein the additional light source is arranged to be turned on during the detection of each of the images.

9. The device according to claim 1, wherein the device additionally comprises:
   a processing unit which is adapted to recognize on the images of the image sequence individual imaged light reflections, and their displacement along the image sequence.

10. A method for automatically detecting the position of an intraocular lens or a natural lens in an eye on the basis of an image sequence,
    the method comprising:
    continuous focusing by an eye of a single visually recognizable reference point during a capturing of an image;
    recognition of individual imaged light reflections and their displacement along an image sequence;
    assigning at least one of the light reflections to a Purkinje-reflex by a recognized shape and the displacement of the corresponding light reflections and a predetermined angle of the respectively corresponding light source, which was switched on during the capture of a respective image;
    switching the light sources on and off so that during capture of the images, the light sources are turned on in a predetermined order and that during the capture of each of the images only one predetermined light source is turned on; and
    calculating the decentration and/or tilt of the lens based on the assigned Purkinje reflexes.

11. The method according to claim 10, further comprising:
    automatically recognizing an outline of the pupil and/or iris of the imaged eye in the image sequence.

12. A device for automatically detecting the position of an intraocular lens or a natural lens in an eye, comprising:
    a camera comprising a camera lens and a camera axis;
    a positioning unit adapted to bring the camera relative to the eye to be imaged in a fixed, predetermined position;
    a plurality of individual light sources, which are arranged so that each of the light sources can emit light beams at a respective predetermined angle with respect to the camera axis and in the direction of the eye to be imaged; and
    a control unit which is configured with a constant position of the camera and the light sources, to capture an image sequence of the eye to be imaged and to secure said sequence on a non-transitory storage medium;
    wherein the control unit is configured to switch the light sources on and off so that during capture of the images, the light sources are turned on in a predetermined order and that during the capture of each of the images only one predetermined light source is turned on; and
    wherein the control unit is further configured to recognize individual imaged light reflections and their displacement along the image sequence; assign at least one of the light reflections to a Purkinje-reflex by a recognized shape and the displacement of the corresponding light reflections and the predetermined angle of the respectively corresponding light source, which was switched on during the capture of a respective image; and calculate the decentration and/or tilt of the lens based on the assigned Purkinje reflexes; and wherein the light sources are arranged on a support plate; and wherein the device further comprises a single visually recognizable reference point on the support plate.

* * * * *